US008940275B2

(12) United States Patent  
Huang et al.

(10) Patent No.: US 8,940,275 B2
(45) Date of Patent: Jan. 27, 2015

(54) NANOPARTICLES BASED ON GADOLINIUM COORDINATION POLYMERS AS HIGHLY SENSITIVE T1 MRI CONTRAST AGENTS

(75) Inventors: Songping D. Huang, Kent, OH (US); Yongxiu Li, Kent, OH (US); James P. Basilion, Shaker Heights, OH (US); Jihua Hao, Beachwood, OH (US); Christopher Flask, Avon Lake, OH (US)

(73) Assignees: Kent State University, Kent, OH (US); Case Western Reserve University, Cleveland, OH (US)

( * ) Notice: Subject to any disclaimer, the term of this patent is extended or adjusted under 35 U.S.C. 154(b) by 0 days.

(21) Appl. No.: 13/819,018

(22) PCT Filed: Sep. 8, 2011

(86) PCT No.: PCT/US2011/001559
§ 371 (c)(1),
(2), (4) Date: Feb. 26, 2013

(87) PCT Pub. No.: WO2012/033531
PCT Pub. Date: Mar. 15, 2012

(65) Prior Publication Data
US 2013/0209369 A1  Aug. 15, 2013

Related U.S. Application Data

(60) Provisional application No. 61/381,699, filed on Sep. 10, 2010.

(51) Int. Cl.
*A61B 5/055* (2006.01)
*A61K 49/08* (2006.01)
*A61K 49/06* (2006.01)
*A61B 6/00* (2006.01)
*A61K 49/18* (2006.01)

(52) U.S. Cl.
CPC .............. *A61K 49/08* (2013.01); *A61K 49/06* (2013.01); *A61B 6/481* (2013.01); *A61K 49/18* (2013.01); *A61B 5/055* (2013.01)
USPC .................................................. 424/9.322

(58) Field of Classification Search
None
See application file for complete search history.

(56) References Cited

U.S. PATENT DOCUMENTS

2008/0014149 A1  1/2008  Murthy et al.
2009/0110644 A1  4/2009  Margel et al.

OTHER PUBLICATIONS

Chelabaeva, E., et al., Mesoporous Silicananoparticles Combining Two-Photon Excited Fluorescence and Magnetic Properties, J. Mater. Chem. vol. 20, Jan. 26, 2010, pp. 1877-1884.
Mullica, D., et al., Gadolinium Potassium Hexacyanoferrate(II) Trihydrate, Acta Cryst., Section C, 1996, pp. 2956-2959.

*Primary Examiner* — Paul Dickinson
(74) *Attorney, Agent, or Firm* — Hudak, Shunk & Farine Co. LPA

(57) ABSTRACT

An agent for imaging of a biological system or delivering drugs to a biological system including one or more nanoparticles formed of at least one gadolinium coordination polymer.

22 Claims, 3 Drawing Sheets

[Gd(DTPA)(H$_2$O)]$^{2-}$ (Magnevist™)

[Gd(DTPA-BMA)(H$_2$O)] (Omniscan™)

[Gd(BOPTA)(H$_2$O)]$^{2-}$ (MultiHance™)

[Gd(DTPA-BMEA)(H$_2$O)] (OptiMARK™)

[Gd(DOTA)(H$_2$O)] (Dortarem™)

[Gd(HP-DO3A)H$_2$O)] (ProHence™)

[Gd(DO3A-butrol)H$_2$O)] (Gadovist™)

US 8,940,275 B2

NANOPARTICLES BASED ON GADOLINIUM COORDINATION POLYMERS AS HIGHLY SENSITIVE T1 MRI CONTRAST AGENTS

CROSS-REFERENCE

This application claims the priority filing date of U.S. Provisional Application Ser. No. 61/381,699 filed Sep. 10, 2010, herein fully incorporated by reference.

FIELD OF THE INVENTION

The invention relates generally to contrast agents used in medical imaging applications, and more particularly to MRI contrast agents and drug delivery platform created from nanoparticles based on gadolinium coordination polymers. More specifically, MRI contrast agents generally have the chemical formula $AGd[Fe^{II}(CN)_6]nH_2O$ where A is $Li^+$, $Na^+$, $K^+$, $Rb^+$, $Cs^+$, $NH_4^+$, or $Tl^+$; and n is 1-10, or the chemical formula $Gd[M^{III}(CN)_6].nH_2O$ where M is Cr, Mn, Fe, Co or Ru, where n is 1-10.

BACKGROUND OF THE INVENTION

Medical imaging modalities allow the visualization of the organs within a human body. For example, computed tomography (CT) also known as computed axial tomography (CAT), employs X-rays to produce 3 D images. There are tens to hundreds of millions of scans done annually worldwide. Although non-invasive, CT is regarded as a moderate to high radiation diagnostic technique.

Another example of medical imaging technology is positron emission tomography (PET) and single photon emission computed tomography (SPECT). PET and SPECT use a short-lived radioactive isotope that undergoes a decay to emit a positron or gamma rays. There are tens to hundreds of millions of diagnostic medical procedures done every year. Both techniques expose the patient to low-level radiation and therefore impose risk to the patient.

A further medical imaging technology is magnetic resonance imaging (MRI). MRI uses a powerful magnetic field to align the nuclear magnetization of protons in water. It provides much greater contrast than does CT. Again, many millions of MRI exams are given annually.

Magnetic resonance imaging (hereinafter referred to as "MRI") has emerged as a prominent noninvasive diagnostic tool in clinical medicine and biomedical research. Among its many advantages, MRI can produce images with large contrast to visualize the structure and function of the body. It provides detailed images of the body in any plane. MRI generally provides much greater contrast between different soft tissues of the body as compared to other techniques, making it particularly useful in musculoskeletal imaging, cardiovascular and vascular imaging, neurological imaging, oncological imaging and other body parts or functions and diseases. Unlike CT or PET, MRI uses no ionizing radiation, but instead uses a magnetic field to align the nuclear magnetization of atoms (usually hydrogen atoms) in the body. The MRI imaging techniques therefore provide high quality images without exposing the patient to any kind of harmful radiation. The diagnostic power of MRI can be further enhanced with the use of a contrast agent. It is estimated that about 35% of all clinical MRI diagnostic examinations are performed with the intravenous injection of a contrast agent. This constitutes millions of doses of MRI contrast agent administered worldwide annually.

In magnetic resonance imaging (MRI) an image of an organ or tissue is obtained by placing a subject in a strong magnetic field and observing the interactions between the magnetic spins of the protons and radiofrequency electromagnetic radiation. The magnetic spins produce an oscillating magnetic field which induces a small current in the receiver coil, wherein this signal is called the free induction decay (FID). Two parameters, termed proton relaxation times, are of primary importance in the generation of the image. They are called $T_1$ (also called the spin-lattice or longitudinal relaxation time) and $T_2$ (the spin-spin or transverse relaxation time). The time constant for the observed decay of the FID is called the T2* relaxation time, and is always shorter than $T_2$. The $T_1$, $T_2$ and $T_2$* relaxation times depend on the chemical and physical environment of protons in various organs or tissues.

In some situations or tissues, the MRI image produced may lack definition and clarity due to a similarity of the signal from different tissues or different compartments within a tissue. In some cases, the magnitude of these differences is small, limiting the diagnostic effectiveness of MRI imaging. Image contrast is created by differences in the strength of the MRI signal recovered from different locations within the tissue or sample. This depends upon the relative density of excited nuclei (such as water protons), on differences in the relaxation times $T_1$, $T_2$ and $T_2$* of those nuclei. The type of imaging pulse sequence may also affect contrast. The ability to choose different contrast mechanisms gives MRI tremendous flexibility. In some situations, the contrast generated may not adequately show the tissues, anatomy or pathology as desired, and a contrast agent may enhance such contrast. Thus, there exists a need for improving image quality through the use of contrast agents.

Contrast agents are substances which exert an effect on the nuclear magnetic resonance (NMR) parameters of various chemical species around them. Ordinarily, these effects are strongest on the species closest to the agent, and decrease as the distance from the agent is increased. Thus, the areas closest to the agent will possess NMR parameters which are different from those further away. Proper choice of a contrast agent will, theoretically, result in uptake by only a certain portion of the organ or a certain type of tissue (e.g., diseased tissues), thus providing an enhancement of the contrast, which in turn generates a more accurate image. Contrast agents for MRI that are available may be injected intravenously to enhance the appearance of tumors, blood vessels and/or inflammation for example. Contrast agents may also be directly injected into a joint, for MR images of joints, referred to as arthrograms. Contrast agents may also be taken orally for some imaging techniques. Contrast agents generally work by altering the relaxation parameters, $T_1$, $T_2$ or $T_2$*, such as by shortening these relaxation times.

Since MRI images can be generated from an analysis of the $T_1$, $T_2$ or $T_2$* parameters discussed above, it is desirable to have a contrast agent which affects either or both parameters. Much research has, therefore, centered around two general classes of magnetically active materials: paramagnetic materials (which act primarily to decrease $T_1$) and ferromagnetic materials (which act primarily to decrease $T_2$).

Paramagnetism occurs in materials that contain unpaired electrons which do not interact and are not coupled. Paramagnetic materials are characterized by a weak magnetic susceptibility, where susceptibility is the degree of response to an applied magnetic field. They become weakly magnetic in the presence of a magnetic field, and rapidly lose such activity (i.e., demagnetize) once the external field is removed. It has long been recognized that the addition of paramagnetic solutes to water causes a decrease in the $T_1$ parameter.

Because of such effects on $T_1$ a number of paramagnetic materials have been used as NMR contrast agents. However, a major problem with the use of contrast agents for imaging is that many of the paramagnetic and ferromagnetic materials exert toxic effects on biological systems making them inappropriate for in vivo use. Because of problems inherent with the use of many presently available contrast agents, there exists a need for new agents adaptable for clinical use. In order to be suitable for in vivo diagnostic use, such agents must combine low toxicity with an array of properties including superior contrasting ability, ease of administration, specific biodistribution (permitting a variety of organs to be targeted), and a size sufficiently small to permit free circulation through a subject's vascular system or by blood perfusion (a typical route for delivery of the agent to various organs). Additionally, the agents must be stable in vivo for a sufficient time to permit the clinical study to be accomplished, yet capable of being ultimately metabolized and/or excreted by the subject.

A $T_1$ agent primarily acts to brighten up the tissues where the agent is present due to its ability to enhance the longitudinal relaxation rate of protons from water ($1/T_1$). All the $T_1$ contrast agents currently used in clinical MRI imaging are gadolinium-based paramagnetic complexes with various polyaminopolycarboxylate ligands. Gadolinium (Gd) is a rare-earth metal that can form a stable 3+ ion with 7 unpaired electrons (4 $f^7$, S=7/2), the highest number of unpaired electrons (or magnetic spins) per metal center obtainable by any metallic element in the periodic table. FIG. 1 shows the structures of several typical Gd-based MRI contrast agents approved for clinical applications so far. The most noticeable feature in all these complexes is the water coordination to the metal center, which provides an important mechanism for enhancing the proton's longitudinal relaxation rate for this water and the surrounding water molecules.

Although gadolinium-enhanced tissues and fluids appear brighter on $T_1$-weighted Images, which provides high sensitivity for detection of vascular tissues (e.g. tumors) and permits assessment of brain perfusion (e.g. in stroke), such compounds also have problems and risks. The relaxivity decreases with increasing magnetic field, and thus higher dosages are required to achieve the same contrast with higher magnetic fields. There have been concerns raised regarding the toxicity of gadolinium-based contrast agents and their impact, particularly on people with impaired kidney function. Both the free $Gd^{3+}$ ions and the polyaminopolycarboxylate ligand molecules used to sequester the metal ions exhibit in vivo toxicity. Previously, it was assumed that the formation of a chelate between the metal ions and the ligand molecules with high thermodynamic stability and kinetic inertness can prevent the complexes from falling apart, thus reducing the toxicity. Unfortunately, the complex biochemical, pharmacokinetic and metabolic properties of such chelates often render the in vitro working model based on the thermodynamic and kinetic stability considerations inadequate for predicting their in vivo safe delivery. Use of these compounds has been linked to nephrogenic systemic fibrosis (NSF) and nephrogenic fibrosing dermopathy (NFD) for example. The renal toxicity of such agents has also prompted the US FDA to issue a public health advisory regarding the risk of using such agents. Additionally, such compounds are not possible to take orally, requiring intravenous administration, and do not act intracellularly but only extracellularly, thereby limiting their effectiveness.

The second type of contrast agents (i.e. $T_2$ agents) that have been recently approved for clinical use are from the family of iron oxide nanoparticles as shown in FIG. 2. These include superparamagnetic iron oxides (hereinafter referred to as "SPIO"; 50-500 nm) and ultrasmall superparamagnetic iron oxides (USPIOs; 5-50 nm). In contrast to Gd-based MRI contrast agents, iron oxide nanoparticles can only increase the transverse relaxation rate of protons from water ($1/T_2$), thus producing darkened spots in the tissues where the material is present. From the standpoint of clinical diagnostic imaging, $T_2$ agents produce much less useful information. Thus, the primary application of the $T_2$ agents is for image-guided drug delivery and the monitoring of surgical procedures. Such materials have also been used for liver imaging, as normal liver tissue retains the agent, but abnormal areas (e.g. scars, tumors) do not.

It should be noted that both the Gd-based $T_1$ agents and iron oxide-based $T_2$ agents are unstable in the acidic environment of the stomach, which has prevented them from being ever considered for oral delivery. Consequently, these materials can only be intravenously administered. In order to develop any new $T_1$ agent, the water molecules from the surroundings need to be able to exchange with the inner-sphere water molecules, and reside on the metal sites on and off, which can provide a mechanism to significantly shorten the $T_1$ relaxation time of water's protons, thus increasing the proton's magnetic resonance signal intensity (i.e. imaging contrast).

Detection of disease-related biomarkers and/or the alterations in disease-related gene expressions using MRI modalities represents an important new application of MRI as a cellular and molecular probe for early diagnosis of many diseases (e.g., cancer). This capability can fundamentally change the understanding of diseases by combining molecular information with high resolution imaging. The development of new-generation MRI contrast agents for such applications requires much higher sensitivity (relaxivity) than the current commercial $Gd^{3+}$-chelate-based $T_1$ agents can provide. However, due to artifacts and background interferences caused, the readout of $T_2$ weighted images is usually difficult to interpret. Consequently, their utility is limited for studying biology.

In order for a contrast agent to be effective in enhancing the $T_1$ relaxation of bulk water, at least one water molecule is required to directly coordinate to the paramagnetic metal center for contributing to the $T_1$ inner-sphere relaxation. The great majority of the MRI contrast agents used in clinical imaging consists of the $Gd^{3+}$ Ion chelated by various low molecular weight polyaminopolycarboxylate ligands. The relaxivity of such chelates consists of contributions from both inner-sphere and outer-sphere relaxation mechanisms. Such contributions are strongly correlated to the chelate structure and the dynamics in solution. The mechanism of inner-sphere relaxation in molecular $Gd^{3+}$-chelates is well understood on the basis of the Solomon-Bloembergen-Morgan (hereinafter referred to as "SBM") theory. The inner-sphere relaxation of the small molecule chelates such as the commercial $T_1$ weighted agents is directly proportional to the number of water molecules coordinated to the Gd(III) center:

$$r_{ip}^{is} = \frac{q[C]}{55.6(T_{1M} + \tau_M)} \quad \text{(Eq. 1)}$$

where q is the number of water molecules directly coordinated to the Gd(III) center, [C] is the molar concentration of the contrast agent, $T_{1M}$ is the longitudinal relaxation time of the bound water, and $\tau_M$ is the mean residence life-time of the coordinated water molecule. Currently, commercial $T_1$ contrast agents contain only one water molecule directly coordinated to the Gd)III) center as shown in FIG. 1. This structural feature limits the image enhancement sensitivity of such agents. The $r_1$ values, which are the measure of imaging contrast efficacy, for these commercial contrast agents are very low, i.e., only a few percent of what is the theoretically attainable value predicted by the SBM theory, ranging from 4.2 to 7.3 $mM^{-1}\times_s^{-1}$ at 1.5 T, as shown in Table 1.

TABLE 1

The typical relaxivity values for the clinical MRI contrast agents.

| Trademark | R1 ($mM^{-3}\times_s^{-1}$) |
|---|---|
| Dotarem ® | 4.2 |
| ProHance ® | 4.4 |
| Gadovist ® | 5.3 |
| Magnevist ® | 4.3 |
| Omniscan ® | 4.6 |
| OptiMARK | 5.2 |
| MultiHance | 6.7 |
| Primovist | 7.3 |

Although a higher number of coordination water can lead to large increase in relaxivity, the complex is then highly susceptible to displacement by proteins or biological ligands.

Furthermore, high concentrations (>0.1 mM) are needed for these commercial agents to be effective at the low to moderate magnetic fields, i.e., 0.3 T (12.5 MHz) to 3 T (125 MHz). However, the use of high magnetic-field MR instruments has been steadily increasing in recent years. The high-field scanners can greatly shorten data acquisition time, improve signal-to-noise (hereinafter referred to as "SNR"), and provide high spatial resolution, particularly, high resolution imaging with sufficient contrast that is critical for applications such as vasculature in tumors, brain perfusion in strokes, and blood clots in micro-vessels. Current commercial contrast agents become ineffective at higher magnetic fields.

It would be desirable to provide MRI contrast agents which alleviate concerns with known agents and allows high contrast images to be achieved, with low toxicity. It would also be desirable to provide a MRI contrast agent that provides specific biodistribution, cellular imaging and permits free circulation through a patient's vascular system. Further, the qualities of ease of administration, such as by oral delivery methods, and providing stability in vivo for a sufficient time to permit the clinical study to be accomplished, while being ultimately metabolized and/or excreted by the subject, are needed. It would also be advantageous to provide a contrast agent that may allow both $T_1$ and $T_2$ imaging techniques to be performed.

There is also a need for drug delivery materials that allow drugs or other therapeutic agents to be delivered to tissues or portions of the body in an effective manner. There is also a need for agents that allow drugs or other therapeutic agents to be introduced into cells of the body.

SUMMARY OF THE INVENTION

An embodiment of the present invention includes an agent for imaging of a biological system or delivering drugs to a biological system that includes one or more nanoparticles formed of at least one gadolinium coordination polymer.

An aspect of an embodiment of the present invention includes at least one gadolinium coordination polymer as a 3D polymeric network structure containing a Gd(III) center.

Another aspect of an embodiment of the present invention includes at least one gadolinium coordination polymer further including at least one $CN^-$ group from a hexacyanometallate ligand, such as $[M(CN)_6]^{n-}$ (M=Cr, Mn, Fe, Co and Ru; n=3 or 4).

Yet another aspect of an embodiment of the present invention includes at least one set of six $CN^-$ groups.

An aspect of an embodiment of the present invention includes that at least one gadolinium coordination polymer further includes two water molecules coordinated to the $Gd^{III}$ center.

Another aspect of an embodiment of the present invention includes at least one gadolinium coordination polymer further includes that the at least one octahedral $[Fe^{II}(CN)_6]^{4-}$ block is coordinated to the at least one gadolinium coordination polymer.

Another aspect of an embodiment of the present invention includes at least one gadolinium coordination polymer further includes at least one octahedral $[M^{III}(CN)_6]^{3-}$ (M=Cr, Mn, Fe, Co and Ru) block that is coordinated to at least one gadolinium coordination polymer.

Yet another aspect of an embodiment of the present invention includes at least one gadolinium coordination polymer containing the $Gd^{3+}$ ion.

An aspect of an embodiment of the present invention includes the agent as one or more nanoparticles within the size ranging from about 4 nm to about 100 nm.

Another aspect of an embodiment of the present invention includes the agent as being used as a $T_1$-weighted magnetic resonance imaging contrast agent.

Yet another aspect of an embodiment of the present invention includes the agent with a chemical formula of about $AGd[Fe^{II}(CN)_6]\cdot nH_2O$ ($A=Li^+$, $Na^+$, $K^+$, $Rb^+$, $Cs^+$, $NH_4^+$, $Tl^+$; n=1-10).

Yet another aspect of an embodiment of the present invention includes the agent with a chemical formula $Gd[M^{III}(CN)_6]\cdot nH_2O$ (M=Cr, Mn, Fe, Co and Ru; n=1-10).

An aspect of an embodiment of the present invention includes the agent as belonging to an orthorhombic system, space group Pnma[No. 62] with unit cell parameters of about a=12.632(2) Å, b=13.618 Å, c=7.2249 Å, and V=1242.9(3) Å.

An aspect of an embodiment of the present invention includes the agent as belonging to an orthorhombic system, space group Cmcm [No. 63] with unit cell parameters of about a=7.286(4) Å, b=12.559(5) Å, c=13.619(4) Å, α=90°, β=90° and γ=90°.

An aspect of an embodiment of the present invention includes the agent as belonging to an orthorhombic system, space group Cmcm [No. 63] with unit cell parameters of about a=7.396(3) Å, b=12.837(5) Å, c=13.673(5) Å, α=90°, β=90° and γ=90°.

An aspect of an embodiment of the present invention includes the agent as belonging to a monoclinic space group $C2_1$ [No. 5] with a=12.759(5) Å, b=7.404(3) Å and c=13.654(5) Å, α=90°, β=9.2(2)* and γ=90°.

Yet another aspect of an embodiment of the present invention includes the agent as having a longitudinal and transverse molar relaxivity values of about $r_1$=16.8 $mM^{-1}\times s^{-1}$ and $r_2$=23.9 $mM^{-1}\times_s^{-1}$.

An aspect of an embodiment of the present invention includes the agent as having an $r_2/r_1$ ratio of about 1.4.

Another embodiment of the present invention includes a method for the preparation of an agent of one or more nanoparticles formed of at least one gadolinium coordination polymer including the steps of combining a concentration of a gadolinium ion ($Gd^{3+}$) with a soluble hexacyanometallate $[M(CN)_6]^{n-}$ ligand.

Yet another embodiment of the present invention includes a method for the preparation of an agent of one or more nanoparticles formed of at least one gadolinium coordination polymer including the steps of combining a concentration of $GdCl_3$ with $K_4[Fe(CN)_6]$.

A contrast agent composition comprises a plurality of polymer nanoparticles having the formula $AGd[Fe^{II}(CN)_6] \cdot nH_2O$, where A is $Li^+$, $Na^+$, $K^+$, $Rb^+$, $Cs^+$, $NH_4^+$ or $Tl^+$ and wherein n is from 1 to about 10; or having the formula $Gd[M^{III}(CN)_6] \cdot nH_2O$ wherein M is Cr, Mn, Fe, Co, or Ru and n is from 1 to about 10.

These and other advantages and novel features of the claimed invention, as well as details of illustrated embodiments thereof, will be more fully understood from the following description and drawings.

DETAILED DESCRIPTION OF THE INVENTION

Figure 1:
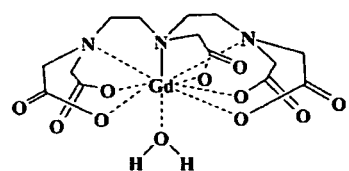
FIG. 1 illustrates structures of various commercial $T_1$ MRI contrast agents.
Figure 1:
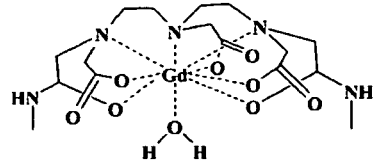
Figure 1:
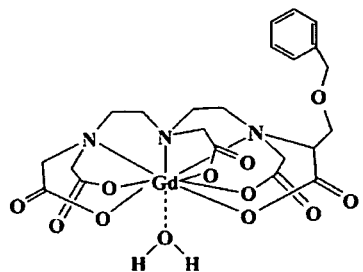
Figure 1:
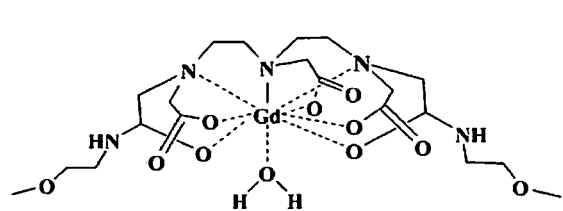
Figure 1:
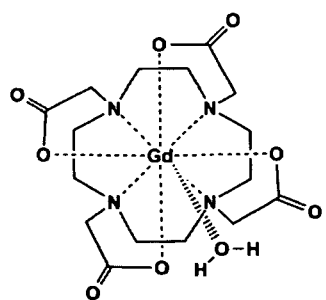
Figure 1:
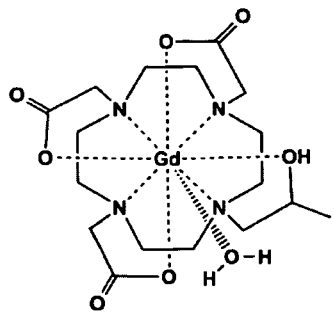
Figure 1:
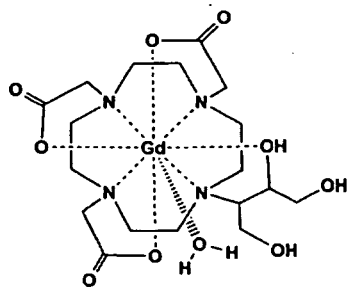
Figure 2:
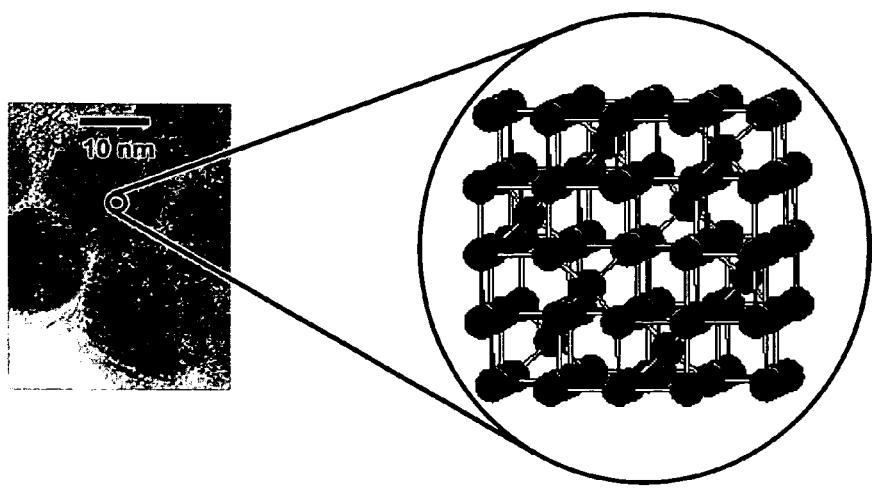
FIG. 2 illustrates a crystal structure of $KGd[Fe^{II}(CN)_6] \cdot 3H_2O$ showing two coordinated water molecules to $Gd^{3+}$.

The present invention relates to gadolinium coordination polymer (hereinafter referred to as "GdCP") nanoparticles as contrast agents for medical imaging or as vehicles for drug delivery, and methods relating to the use thereof.

In an embodiment of the present invention, a coordination polymer formed between the $Gd^{3+}$ ion and the hexacyanometallate $[M(CN)_6]^{n-}$ as a nanoparticle platform. The compound may have certain characteristics such as 1) the $[M(CN)_6]^{n-}$ being a remarkably stable ligand against dissociating into $M^{n+}$ and $CN^-$ ions due to strong ligand-field effect of the $CN^-$ group in combination with the low-spin electron configuration of the metal center, which gives rise to a maximum ligand-field stabilization (hereinafter referred to as "LFS"), 2) upon forming the coordination polymer with an extended network structure, the high lattice energy of such 3D structure will lock both the $Gd^{3+}$ and $CN^-$ ions in their lattice positions in order to prevent the metal and ligand ions from leaching into the solution or from undergoing transmetallation reactions, and 3) the formed coordination polymer may belong to a large class of metal-organic frameworks (hereinafter referred to as "MOFs") that are usually porous and crystalline compounds with water molecules filling the structural cavities or even coordinating to the metal centers, thus providing an active inner-sphere relaxation mechanism as seen in solid-state compounds.

Preparation of the gadolinium nanoparticles of the present invention are generally be prepared in accordance with the following formula $GdX_3 + A_4[Fe(Cn)_6] \rightarrow AGd[Fe^{II}CN_6] \cdot nH_2O$, where X is F, Cl, or I, with Cl being preferred, and A is $Li^+$, $Na^+$, $K^+$, $Rb^+$, $Cs^+$, $NH^{4+}$, or $Tl^+$. The reaction was carried out in an aqueous solution and the above-noted reaction is unknown to the art and to the literature. The reaction temperature is ambient, that is from about 10 to about 40° C. and preferably from about 20 to about 30° C. and is generally carried out in the earth's atmosphere. The reaction time can be anywhere from about 1 to about 5 hours with from about 2 to about 4 hours being desired. The mole ratio of the GdX compound to the $A_4[Fe(CN)_6]$ compound is generally from about 1 to about 1.

The gadolinium contrast agent of the present invention is generally applied to an animal such as a human as dispersed nanoparticles in water stabilized by a hydrophilic coating comprising a carboxylic acid and a hydrophilic biocompatible polymer. The suitable carboxylic acid can include, but are not limited to, common carboxylic acids such as acetic acid, oxalic acid, citric acid, tartaric acid, adipic acid, gluconic acid, and other mono-, di-, tri- or polycarboxylic acids. Furthermore, the suitable hydrophilic biocompatible polymer used for coating to prolong blood circulation times, reduced biological toxicity and particle solution stability against aggregation can include, but are not, limited to polyethylene glycol (PEG), polyvinylpyrrolidone (PVP) or other polysaccharides.

An example of the preparation of a nanoparticle gadolinium contrast agents of the present invention is as follows. A 100-mL aqueous solution of $GdCl_3$ (1 mM) was added dropwise into an aqueous 100-mL solution of $K_4[Fe(CN)_6]$ (1 mM) containing 250 mg of polyvinylpyrrolidone (PVP, MW=8000) under vigorous stirring. The resulting solution was further stirred at room temperature for ca. 3 hrs. The sample was dialyzed using regenerated cellulose tubular membrane (MWCO=3500) against distilled water for two days.

Figure 3:
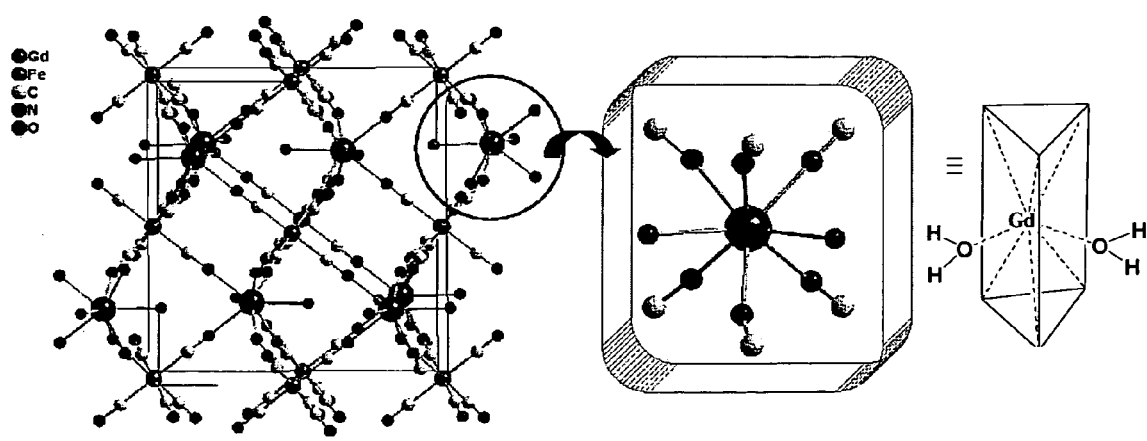
FIG. 3 illustrates a crystal structure of $KGd[Fe^{II}(CN)_6] \cdot 3H_2O$ with $K^+$ ions and water molecules inside the structural cavity removed for clarity.

X-ray structures of nanoparticles of the general composition $KGd[Fe^{II}(CN)_6] \cdot nH_2O$ (n=3-5) may be determined by the powder diffraction method. This compound crystallizes in the orthorhombic space group with a=12.6098 (4) Å, b=13.6161(4) Å and c=7.2490(3) Å (space group Pnma) and has a 3D extended polymeric network structure with two water molecules directly coordinated to the Gd(III) center, as shown in FIG. 3. The presence of one zeolitic and two coordinated water molecules in the structure were also confirmed by thermogravimetric analysis (hereinafter referred to as "TGA") and Fourier Transform infrared detection (hereinafter referred to as "FT-IR"). Moreover, leaching of $Gd^{3+}$ ions was measured in the pH range of 0 to 7 in distilled water, saline solution, and PBS, respectively, using inductively coupled plasma optical emission spectrometry (hereinafter referred to as "ICP-OES"). The highest concentration of free $Gd^{3+}$ ions was found to be ~53 µg/mL (i.e. ~53 parts per billion at pH=0), after 24 hours of incubation. The release of free cyanide ions were also measured using a Merckoquant® Cyanide Test. After incubating the nanoparticles with distilled water at pH=7, 5, 3, and 1 or the saline solution at pH=7.3 between four to twenty four hours, all the solutions that were tested showed a free cyanide concentration below the detection limit of ~0.1 mg/L (or ~0.1 ppm). Assuming that the average blood volume of 5.3 L, in a male adult, is injected with 0.53 L (10% of the total blood volume) of the nanoparticles at the concentration of 5 mM, a concentration approximately ten times higher than that required for clinical MR imaging, the estimated total amount of free cyanide ions released to the body may be less than or equal to 0.53 mg. The latter is about twenty seven times below the minimal toxic dose (14.4 mg) or more than 100 times below the minimal lethal dose (56 mg) in humans. The concentration of free cyanide ions in the blood after injection of the gadolinium polymer nanoparticles would even be lower than the blood cyanide concentrations of cigarette smokers (~0.2 mg/L) after smoking a cigarette, or below the maximum contamination level of 0.2 mg/L for cyanide in drinking water established by the Environmental Protection Agency (hereinafter referred to as "EPA").

Figure 4:
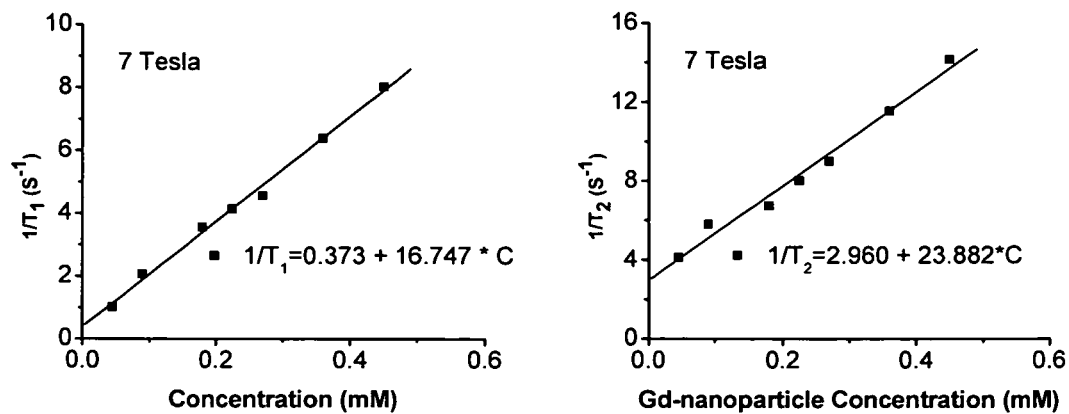
FIG. 4 illustrates $T_1$ (left) and $T_2$ (right) relaxation time measurements on a 7.0-T scanner.

The longitudinal and transverse molar relaxivity values may then be measured using a 7-T Bruker Biospec small animal MRI system to be $r_1=16.8$ mM$^{-1} \times_s^{-1}$ and $r_2=23.9$ mM$^{-1} \times_s^{-1}$, as shown in FIG. 4. The $r_1$ value may be 9-10 times larger than that of Magnevist® at the same magnetic field, demonstrating enhanced qualities over current MRI contrast agents. The lower the $r_2/r_1$ ratio, the less likely that $T_2$ relaxation will interfere with $T_1$ relaxation at the higher magnetic field or with higher concentration of the agent present. An embodiment of the present invention may have an $r_2/r_1$ ratio of 1.4, which is astonishingly low and approaches the theoretical limit of unity. The $r_2/r_1$ ratio also demonstrates why SPIO contrast agents cannot function as an effective $T_1$ agent despite their high $r_1$ values (~10 mM$^{-1} \times s^{-1}$) because their $r_2/r_1$ ratios are larger than 10, as shown in Table 2. Given the combination of the high $r_1$ value and low $r_2/r_1$ ratio found in GdCP, the current platform outperforms other commercial MRI contrast agents.

TABLE 2

Comparison of $r_1$, $r_2$, and $r_2/r_1$ ratios between GdCP and two commercial MRI contrast agents.

| Trademark | $r_1$ (mM$^{-1} \times$ s$^{-1}$) | $r_2$ (mM$^{-1} \times$ s$^{-1}$) | $r_2/r_1$ ratio |
|---|---|---|---|
| Feridex ® (γ-Fe$_2$O$_3$ core) | 10 | 104 | 10.4 |
| Magnevist ® | 4.3 | 4.5 | 1.0 |
| GdCP (current Platform) | 17 | 24 | 1.4 |

Figure 5:
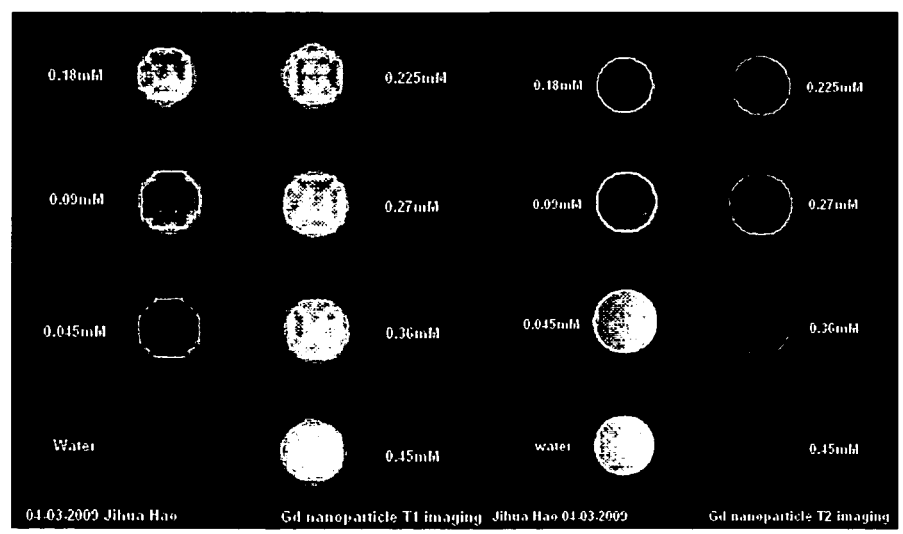
FIG. 5 illustrates MRI slices for $T_1$ (left) and $T_2$ (right) phantoms of GdCP nanoparticles in phosphate buffered saline (hereinafter referred to as "PBS").

With reference to FIG. 5, MRI slices of phantoms consisting of GdCP nanoparticle suspensions in PBS with various concentrations on a 7.0 T scanner revealed that the GdCP agent can perform image contrast enhancements at the μM level on a 7.0 T scanner. Moreover, commercial $T_1$ contrast agents are ineffective even at greater mM levels using a 7.0 T scanner.

As should be clear, in addition to [Fe(CN)$_6$] block, several other hexacyanometallate [M(CN)$_6$] (M=Cr, Mn, Co and Ru) blocks can also be incorporated into the gadolinium polymer to form stable MRI contrast agents. In other aspects and embodiments of the present invention, the one or more nanoparticles are within the size ranging from about 4 nm to about 100 nm for example. The at least one nanoparticle may also be formed of at least one gadolinium coordination polymer may include at least one octahedral [Fe$^{II}$(CN)$_6$]$^{4-}$ block that is coordinated to the at least one gadolinium coordination polymer. Alternatively, the at least one gadolinium coordination polymer may further include at least one octahedral [M$^{III}$(CN)$_6$]$^{3-}$ (M=Cr, Mn, Fe, Co and Ru) block that is coordinated to the at least one gadolinium coordination polymer. The at least one gadolinium coordination polymer may further contain the Gd$^{3+}$ ion, or at least one CN$^-$ group. In an example, the gadolinium coordination polymer may include at least one set of six CN$^-$ groups. Alternatively, the at least one gadolinium coordination polymer may further include two water molecules coordinated to the Gd$^{3+}$ ion. In examples, the agent may have a chemical formula of about AGd[Fe$^{II}$(CN)$_6$]nH$_2$O (A=Li$^+$, Na$^+$, K$^+$, Rb$^+$, Cs$^+$, NH$_4$+, Tl$^+$; n=1-10), that is A can be any of Li$^+$, Na$^+$, K$^+$, Rb$^+$, Cs$^+$, NH$_4$+, or Tl$^+$, and n can be from 1 to about 10, or with a chemical formula Gd[M$^{III}$(CN)$_6$].nH$_2$O (M=Cr, Mn, Fe, Co and Ru; n=1-10), that is M can be any of Cr, Mn, Fe, Co and Ru, and n can be from 1 to about 10. The agent may belong to an orthorhombic system, space group Pnma[No. 62] with unit cell parameters of about a=12.632(2) Å, b=13.618 Å, c=7.2249 Å, and V=1242.9(3) Å, an orthorhombic system, space group Cmcm [No. 63] with unit cell parameters of about a=7.286(4) Å, b=12.559(5) Å, c=13.619(4) Å, α=90°, β=90° and γ=90°, or an orthorhombic system, space group Cmcm [No. 63] with unit cell parameters of about a=7.396(3) Å, b=12.837(5) Å, c=13.673(5) Å, α=90°, β=90° and γ=90°. Also, the agent may belong to a monoclinic space group C2$_1$ [No. 5] with a=12.759(5) Å, b=7.404(3) Å and c=13.654(5) Å, α=90°, β=9.2(2)° and γ=90°. The combination of the space group with the unit cell parameters together defines a specific structure, and the composition can be different or identical. These examples of four structural definition statements relate to possible gadolinium polymers that can be prepared in this class of materials.

Another aspect of embodiments include the agent as having a longitudinal and transverse molar relaxivity values of about $r_1=15$ mM$^{-1} \times_s^{-1}$ and $r_2=25$ mM$^{-1} \times_s^{-1}$ for example, or even further transverse molar relaxivity values of about $r_1=16.8$ mM$^{-1} \times_s^{-1}$ and $r_2=23.9$ mM$^{-1} \times_s^{-1}$. The agent may have an $r_2/r_1$ ratio of about 1.2 to 1.6 and more particularly about 1.4.

The concentration of the gadolinium nanoparticles in water for administration to an animal or human intravenously or orally is from about 1.0 micromoles to about 100 millimoles, desirably from about 10 micromoles to about 80 millimoles, and preferably from about 50 micromoles to about 50 millimoles per liter of solution. The particle size of the gadolinium nanoparticles of the present invention is generally from about 4 to about 100 nanometers, desirably from about 5 to about 80 nanometers, and preferably from about 6 to about 50 nanometers. The in vitro $T_1$ relaxity value, $r_1$ is from about 1.0 to about 100, and desirably from about 4.0 to about 80 mM$^{-1} \times$ s$^{-1}$/mM of Gd ions. The gadolinium contrast agent aqueous solutions are generally stable in acidic to neutral solutions with a pH value from about 1 to about 7.5, desirably from about 2.5 to about 7.5, and preferably from about 3.5 to about 7.3.

For purposes of this invention, the chemical elements are identified in accordance with the Periodic Table of the Elements.

The materials and methods as described above are not to be construed as limiting the invention to any certain application or example. The contrast agent and imaging method, or drug delivery materials or methods disclosed herein may also be used for other medical imaging techniques, drug delivery applications, or other clinical diagnostic applications and biomedical research applications.

While in accordance with the patent statutes the best mode and preferred embodiment have been set forth, the scope of the invention is not intended to be limited thereto, but only by the scope of the attached claims.

What is claimed is:
1. A contrast agent comprising:
one or more gadolinium nanoparticles derived from a compound having the formula AGd[Fe$^{II}$(CN)$_6$].nH$_2$O where A is Li$^+$, Na$^+$, K$^+$, Rb$^+$, C$_s^+$, NH$_4^+$, or Tl$^+$ and wherein n is from 1 to about 10, or Gd[M$^{III}$(CN)$_6$].nH$_2$O where M is Cr, Mn, Fe, Co or Ru, and where n is from 1 to about 10, or both; and said one or more gadolinium nanoparticles having a coating thereon comprising a hydrophilic biocompatible polymer and a carboxylic acid, said coated gadolinium nanoparticles being soluble in water.

2. The contrast agent of claim 1, wherein said at least one gadolinium nanoparticle is a 3D polymeric network structure containing a $Gd^{(III)}$ center.

3. The contrast agent of claim 1, wherein said at least one gadolinium nanoparticle comprises at least one $CN^-$ group derived from a hexacyanometallate ligand, and wherein said biocompatible polymer coating comprises polyethylene glycol, a polysaccharide, or polyvinyl-pyrrolidone, or any combination thereof.

4. The contrast agent of claim 3, wherein said contrast agent has a $r_2/r_1$ ratio of from about 1.2 to about 1.6.

5. The contrast agent of claim 4, wherein said at least one gadolinium nanoparticle further comprises two water molecules coordinated to the $Gd^{(III)}$ center.

6. The contrast agent of claim 2, wherein said at least one gadolinium nanoparticle further comprises at least one octahedral $[M(CN)_6]^{n-}$ where M is Cr, Mn, Fe, Co or Ru block that is coordinated to said biocompatible polymer and wherein said polymer is polyvinylpyrrolidone.

7. The contrast agent of claim 1, wherein said agent is used as a $T_1$-weighted magnetic resonance imaging contrast agent.

8. The contrast agent of claim 1, wherein said agent belongs to an orthorhombic system, space group Pnma with cell parameters of about a=12.632(2) Å, b=13.618 Å, c=7.2249 Å, and V=1242.9(3) Å$^3$.

9. The contrast agent of claim 1, wherein said agent belongs to an orthorhombic space group Cmcm (No. 63) with unit cell parameters of about a=7.286(4) Å, b=12.559(5) Å, c=13.619(4) Å, α=90°, β=90 and γ=90°.

10. The contrast agent of claim 1, wherein said agent belongs to an orthorhombic space group Cmcm (No. 63) with unit cell parameters of about a=7.396(3) Å, b=12.837(5) Å, c=13.673(5) Å, α=90°, β=90° and γ=90°.

11. The contrast agent of claim 1, wherein said agent belongs to a monoclinic space group $C2_1$ (No. 5) with unit cell parameters of about a=12.759(5) Å, b=7.404(3) Å, c=13.654(5) Å, α=90°, β=9.2(2)° and γ=90°.

12. A method for the preparation of the contrast agent of claim 1 comprising: a plurality of gadolinium nanoparticles, said process comprising the steps of:
combining a concentration of an aqueous solution of a gadolinium ion ($Gd^{III}$) with a soluble hexacyanometallate $[M(CN)_6] \cdot H_2O$ where M is Cr, Mn, Fe, Co or Ru; and where n is 1 to 10) in the presence of a hydrophilic biocompatible polymer and forming a plurality of water soluble hydrophilic biocompatible coated gadolinium nanoparticles.

13. A method for the preparation of a contrast agent comprising gadolinium nanoparticles, said process comprising the step of:
reacting an aqueous solution of $GdCl_3$ with $K_4[Fe(CN)_6]$ in the presence of a hydrophilic biocompatible polymer.

14. A contrast agent composition, comprising:
a plurality of nanoparticles derived from a compound having the formula $AGd[Fe^{II}(CN)_6] \cdot nH_2O$, where A is $Li^+$, $Na^+$, $K^+$, $Rb^+$, $Cs^+$, $NH_4+$, or $Tl^+$; and wherein n is from about 1 to about 10, or having the formula $Gd[M^{III}(CN)_6] \cdot nH_2O$ wherein M is Cr, Mn, Fe, Co, or Ru, wherein n is from 1 to about 10, or both; said nanoparticles containing a hydrophilic biocompatible polymer coating and being soluble in water.

15. The contrast agent of claim 14, wherein said nanoparticles have a diameter of from about 4 to about 100 nanometers; and wherein the concentration of said nanoparticles in water is from about 1.0 micromole to about 100 millimoles per liter of solution.

16. The contrast agent of claim 15, wherein said nanoparticles are stable in a solution having a pH value of from about 1 to about 7.5; and wherein said nanoparticles have an in vitro $T_1$ relaxivity value, $r_1$ of from about 1.0 to about 100 mM$^{-1}\cdot$s$^{-1}$/mM of $Gd^{+1}$ ions.

17. The contrast agent of claim 16, wherein said nanoparticle diameter is from about 5 to about 80 nanometers.

18. The contrast agent of claim 17, wherein the concentration of said nanoparticles in water is from about 50 micromoles to about 50 millimoles per liter of solution; wherein said nanoparticle solution has a pH of from about 3.5 to about 7.3; wherein said nanoparticles have an in vitro $T_1$ relaxivity value, $r_1$ of from about 4 to about 80 mM$^{-1}\cdot$s$^{-1}$/mM of $Gd^{+1}$ ions; and wherein said nanoparticle diameter is from about 6 to about 50 nanometers.

19. The contrast agent of claim 14, wherein hydrophilic coating comprises a polyethylene glycol, a polysaccharide, or polyvinylpyrrolidone, or any combination thereof.

20. A process for producing the contrast agent of claim 1 comprising the step of reacting $GdX_3$ with $A_4[Fe(CN)_6]$ in an aqueous solution in the presence of hydrophilic biocompatible polymer to produce a compound having the formula $AGd[Fe^{II}CN_6] \cdot nH_2O$, wherein X is Cl, F, or I, and wherein A is $Li^+$, $Na^+$, $K^+$, $Rb^+$, $Cs^+$, $NH^4+$, or $Tl^+$, and n is from about 1 to about 10, and wherein said gadolinium contrast agent is coated with said biocompatible polymer and is soluble in water.

21. The process of claim 20, wherein said reaction product has a particle size of from about 4 to about 100 nanometers, and wherein said reaction is carried out at ambient temperature.

22. The process of claim 21, wherein the particle size of said reaction product is from about 5 to 80 nanometers, wherein X is Cl, wherein A is K, and wherein said reactant has an in vitro $T_1$ relaxivity value, $r_1$ of from about 1.0 to about 100 mM$^{-1}\cdot$s$^{-1}$/mM of $Gd^{+1}$ ions, and wherein said biocompatible polymer comprises polyethylene glycol, a polysaccharide, or polyvinylpyrrolidone, or any combination thereof.

* * * * *